United States Patent [19]

Cody et al.

[11] Patent Number: 5,022,266
[45] Date of Patent: Jun. 11, 1991

[54] PASSIVE ACOUSTICS PROCESS TO MONITOR FLUIDIZED BED FLOW

[75] Inventors: George D. Cody, Princeton, N.J.; Eugene R. Elzinga, Jr., Marquette, Mich.; Charles L. Baker, Jr., Morris Plains, N.J.

[73] Assignee: Exxon Research and Engineering Company, Florham Park, N.J.

[21] Appl. No.: 318,102

[22] Filed: Mar. 2, 1989

[51] Int. Cl.$^5$ .............................................. G01N 29/00
[52] U.S. Cl. ..................................... 73/579; 73/602; 73/290 V
[58] Field of Search ................ 73/579, 602, 587, 590, 73/592, 584, 861.18, 861.21, 290 V; 201/1

[56] References Cited

U.S. PATENT DOCUMENTS

| | | | |
|---|---|---|---|
| 3,012,848 | 12/1961 | Levey, Jr. et al. | 73/579 |
| 3,553,636 | 1/1971 | Baird | 73/584 |
| 4,357,603 | 11/1982 | Roach et al. | 73/861.21 |
| 4,824,016 | 4/1989 | Cody et al. | 239/8 |

Primary Examiner—Hezron E. Williams
Assistant Examiner—Louis M. Arana
Attorney, Agent, or Firm—Ronald D. Hantman

[57] ABSTRACT

A method for the non-intrusive determination of flow anisotropy through the cross-section of a two phase fluid bed reactor.

5 Claims, 11 Drawing Sheets

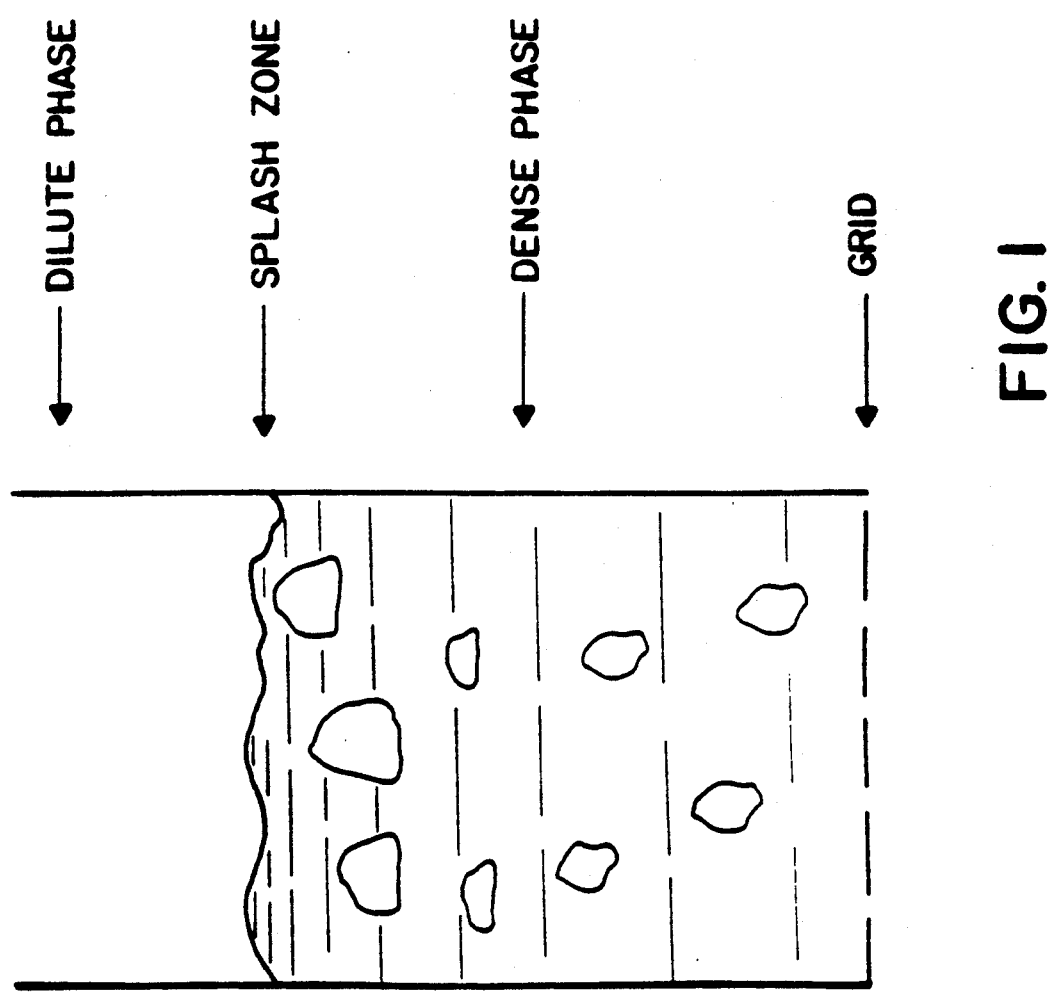
FIG. I

PASSIVE ACOUSTICS PROCESS TO MONITOR FLUIDIZED BED FLOW

BACKGROUND OF THE INVENTION

A fluidized bed is a suspension of solid particles in a stream of gas or liquid of sufficient velocity to support the particle by flow forces against the downward force of gravity Fluidized beds are critical components of important petrochemical processing units such as the catalytic cracking ("cat-cracking") of petroleum on catalytic particles to produce lighter and more valuable products as well as thermal cracking of heavy feeds on coke particles ("fluid bed cokers" or "flexi-cokers") to again produce lighter and more valuable feeds In cat-cracking the regenerator where coke is burned off the catalyst to produce "fresh catalyst" contains a fluidized bed The particles in the fluidized bed within the regenerator are approximately 60 micron diameter pellets of a zeolite. In the case of fluid bed-coking or flexi-coking, fluidized beds can be found in the heater, reactor and in the case of flexi-coking, the gasifier. The particles in this case are approximately 100 to 150 micron particles of coke.

Other fluidized beds containing small solids suspended in a gas include advanced coal combustion units where small particles of coal are suspended and burned to produce heat with minimum pollution and maximum efficiency. Yet another example is found in separation processes in the chemical industry where a fine suspension of particles is suspended in a flowing liquid. In general, fluidized beds are used in many large scale processes where it is desired to maximize the interaction between the surface of a particle and a surrounding gas or liquid.

Fluidized beds can contain volume mass densities for the case of fluid bed cokers and regenerators of the order of 40 pounds per cubic foot and particle velocities of several feet per second. Fluidized beds of the order of 10 to 50 feet in diameter are found in coking and cat cracking. With bed heights of the order of 10 to 60 feet the contained fluids range from less than a hundred to more than a thousand tons of particles. "Gas Fluidization Technology" by Geldart (Wiley 1986) is a review of the technology.

In many cases in the petrochemical industry, the material within the fluidized bed is at an elevated temperature Thus the vessel will often be lined by several inches of refractory. Direct access to the contained particles is thus very difficult. This difficulty is compounded when heavy petroleum feed is being injected into the fluidized bed as in the case of cokers and cat-crackers. Under these circumstances the interior of the fluidized bed can foul any window or probe if special precautions are not taken. Monitoring the flow condition in the fluidized bed is usually limited to static pressure measurements and inferred flow data derived from such measurements. Special precautions to avoid fouling include use of an inert gas to maintain openings in such static pressure measurements and eliminating the pressure drop of the inert gas through a "pressure bridge". While pressure measurements can suggest flow maldistribution within the vessel containing the fluidized bed, they rarely (if at all) pinpoint the region of flow maldistribution.

Flow maldistribution within a fluidized bed can arise from a variety of causes. One example is where the bed is "slumped" in one region of the reactor, greatly reducing the efficiency of the chemical process going on within the fluidized bed. Under conditions of "bed slump", fluidization gas can be channeled to the other side of the reactor, leading to regions of flow turbulence. Under such circumstances excessive attrition of the particles within the fluidized bed can occur leading to an excessive number of fines emitted into the gaseous product of the reactor or into the atmosphere.

Another example where flow maldistribution is a problem is in fluid bed cokers where flow blockage in the region where fluidization steam enters the reactor can lead to a buildup of particle agglomeration and introduce a bed "bogging" condition. Under such circumstances until the flow blockage is eliminated, feed cannot be injected into the coker. Again while pressure or temperature measurements may be useful for identifying the poor flow state of the unit they are seldom useful in identifying the region of the coker reactor on either a vertical or horizontal plane where such a condition exists.

Another example is in the steam stripping section of a catalytic cracking unit (cat-cracker) where hydrocarbon residues on the catalyst are stripped before the spent catalyst is sent to the regenerator for burning off of the coke left from the cracking reaction Efficient stripping has a direct effect on yield of the unit. Under certain circumstances, either flow blockages within the stripping region or large differences in steam input across the stripping region can lead to low efficiency of the stripping reaction. Again it would be desirable to determine the region where a flow maldistribution or blockage is located in order to eliminate it.

Another example is where a critical element of the flow distribution within a fluidized bed is damaged. For example, in many cases flow within the bed is dominated by gas and particle flow through a grid forming the bottom of the dense phase of the bed. Under special circumstances holes in the grid can become blocked, leading to regions of bed slump. Other possibilities include damage to the support structure of the grid due to the large forces exerted by gas pressure across the blocked grid. Under these circumstances a large quantity of a chemically reacting gas may bubble through the bed destroying the uniformity of the process and leading to serious problems in the temperature distribution across the fluidized bed.

In considering all of the above examples where it is desirable to locate the region of flow maldistribution or anisotropy within a fluidized bed it is important to note that it is often equally important to an operator to know that the flow within the fluidized bed is uniform and isotropic. With this information in hand the operator can direct his energies toward other causes of flow, yield, attrition or other problems indicated by global instrumentation such as pressure, temperature or excessive "fines" emitted in the process either into the atmosphere or into the product.

However, if flow maldistribution is occurring within a fluidized bed in a specific region there are a variety of corrective actions that can be taken to remedy the flow maldistribution problem. Steam lancing can be directed toward the region of blockage to clear obstructions. Stripping steam flow can be realigned to produce flow uniformity. In the case of excessive flow of reacting gas through a damaged grid support, "torch oil" can be injected into the unit to reduce gas flow by combustion and hence reduce excessive temperature gradients in regions of the reactor where such gradients would damage components such as cyclones In the most extreme case where a region of the unit has been identified as exhibiting a consistent pattern of flow maldistribution, baffles can be inserted during unit shutdown to produce flow uniformity.

There is a major need to measure the state properties of a fluidized bed non-intrusively from the exterior without penetrating the wall of the vessel and where the traditional use of static pressure gauges is inadequate. The non-intrusive determination of local bed mass density, $P_M$, particle mass, M, and particle velocity, V., and what can be inferred from them as to the flow state of the fluidized bed would be of great value to the operators of such units, in maintaining design performance, improving product yield and trouble shooting poor flow or fluidization conditions within the fluidized bed.

While pressure, temperature and net volume or mass flow are the normal way of monitoring the state of fluidization within a fluidized bed or while a unit is operating, there are a variety of techniques that can be brought to bear on functioning fluidized beds. One example is the use of gamma rays or neutrons to determine the mass density of particles within the vessel. This technique can only be used if the walls and/or diameter of the vessel are less than a critical value since the technique is based on deriving the density from absorption. Too large a vessel diameter, or too thick a wall drops the detected signal below the level of background noise and the mass density cannot be determined. In addition the presence of intense radioactive sources and the necessity to construct elaborate structure to support the detectors of the radiation reduce the use of this technology to elaborate field tests or where major uncertainties arise over the operation of the fluidized beds. The gamma or neutron technique is expensive, has to be scheduled in advance and usually beyond the capability of normal refinery personnel.

Non-intrusive probes that can be used to monitor the flow state of experimental fluidized beds would also be of great value in complementing visual, radiographic and radioactive tracer studies of flow in order to improve or modify existing designs, or for pilot plant studies A current review of a wide variety of electrical, optical, thermal and mechanical technology for studying the hydrodynamics of experimental gas-solid fluidized beds is contained in a recent review by N. P. Cheremisonoff (Ind Eng. Chem Process Dev. 25, 329-351 (1986)). The r ®view presents techniques that are "best suited for laboratory-scale systems, [although-]adaption to industrial pilot facilities and/or commercial units is possible in some cases". However, examination of the presented techniques suggest they suffer from the usual disadvantages of being intrusive, easily contaminated by the process or as in the case of so many of the radioactive techniques severely restricted by environmental or safety considerations.

In the July 1985 issue of the Journal of the American Society of Lubrication Engineers (Lubrication Engineering), J. W. Spencer and D. M. Stevens (of Babcock & Wilcox, a McDermott company of Lynchburg, Va.) describe a technique for "detecting and characterizing particulate matter in fluid flow systems" by using "acoustic emission technology". In this technology the impact of particles generates high frequency surface vibrational waves which are detected as "pulses" by resonant piezo electric transducers. As described in the article, only sensors in contact with probes inserted into the flowing stream correlated with bulk quantity or size of particles in the stream. Sensors mounted non-intrusively on the walls of the pipe "did not correlate well with probe-mounted transducers. Again, this technique is intrusive since it requires penetration of the walls of the vessel (see also U.S. Pat. Nos. 3,816,773 and 4,095,474 which describe similarly intrusive techniques).

A review of the prior art shows that there are no known technologies for reliably and safely measuring or inferring the flow state of two phase flow within a fluidized bed that meet the following criteria:

(1) Non-intrusive and hence requiring neither penetration of the wall or the constructing of external frame works to support radioactive sources and detectors and hence permitting trouble shooting of commercial units;

(2) Non-radioactive and/or suitable for "on-line" monitoring of fluidized beds or transfer lines on working commercial units;

(3) Capable of applying in a "non-intrusive manner" to the refractory lined vessels and transfer lines containing solid particles in the presence of gases such as air, steam and/or volatile hydrocarbons with wall temperatures as high as 250° to 500° C.

SUMMARY OF THE INVENTION

The present invention is a method for the non-intrusive determination of flow anisotropy through the cross-section of a two phase fluid bed in a structure for processing material (hereinafter referred to as a "reactor"). The method includes the steps of measuring reactor wall vibrations of the reactor and then determining the power spectrum as a function of frequency. The wall vibrations are taken at several (first) positions circumferentially about the reactor and the area of the power spectrum under a resonance peak is determined for each of the positions. Then a change in the area of the power spectrum is correlated with a change in flow distribution.

The method may be extended to determine flow anisotropy in the vertical direction by performing the additional steps of measuring reactor wall vibrations of the reactor and then determining the power spectrum as a function of frequency, the wall vibrations taken at several second positions circumferentially about the reactor, the second positions spaced vertically from the first positions about the reactor, determining the area of the power spectrum under a resonance peak for each of the second positions, and comparing a change in the area of the power spectrum between adjacent first positions with the change between the area of the power spectrum between corresponding second positions and correlating difference between the changes in the area of the power spectrum with a change in bed density.

The non-intrusive method tolerates the presence of internal refractory in the vessel containing the fluidized bed and can operate over wide extremes of temperature. It can be clearly distinguished from all active acoustic techniques and has a wider breadth of applications.

The process can be described as a "passive" process since the desired information is obtained from processing vibrational or solid borne sound produced by the process itself.

While the invention is of particular importance with respect to commercial units where there are few if any alternative technologies to measure it will also find use in pilot plant and experimental studies. Although the description is focused on two phase solid/gas flow, the skilled practitioner will realize that it is also applicable to two phase solid/liquid flow.

BRIEF DESCRIPTION OF THE DRAWINGS

FIG. 1 shows a schematic of a fluidized bed in a reactor indicating dense and dilute phase region of bed.

FIG. 3A shows incomplete fluidization in one region of the bed (bed "slump"), FIG. 3B shows normal bubbling in the fluidized bed, and FIG. 3C shows excessive turbulence in the bed arising from poor gas distribution.

FIG. 5(A) shows the signal produced by accelerometer as a function of time, FIG. 5(B) shows the square of the signal produced by the accelerometer as a function of time and the relationship between the mean square acceleration and the area under the power spectrum, and FIG 5(C) shows the power spectrum as a function of frequency.

DESCRIPTION OF THE PREFERRED EMBODIMENT

The present invention is a passive acoustic process to monitor flow distribution in a reactor. The process is intended to permit operation of the reactor under conditions that increase yield as well as to identify regions where mechanical lead to flow maldistribution within the bed for subsequent correction.

Figure 2B:
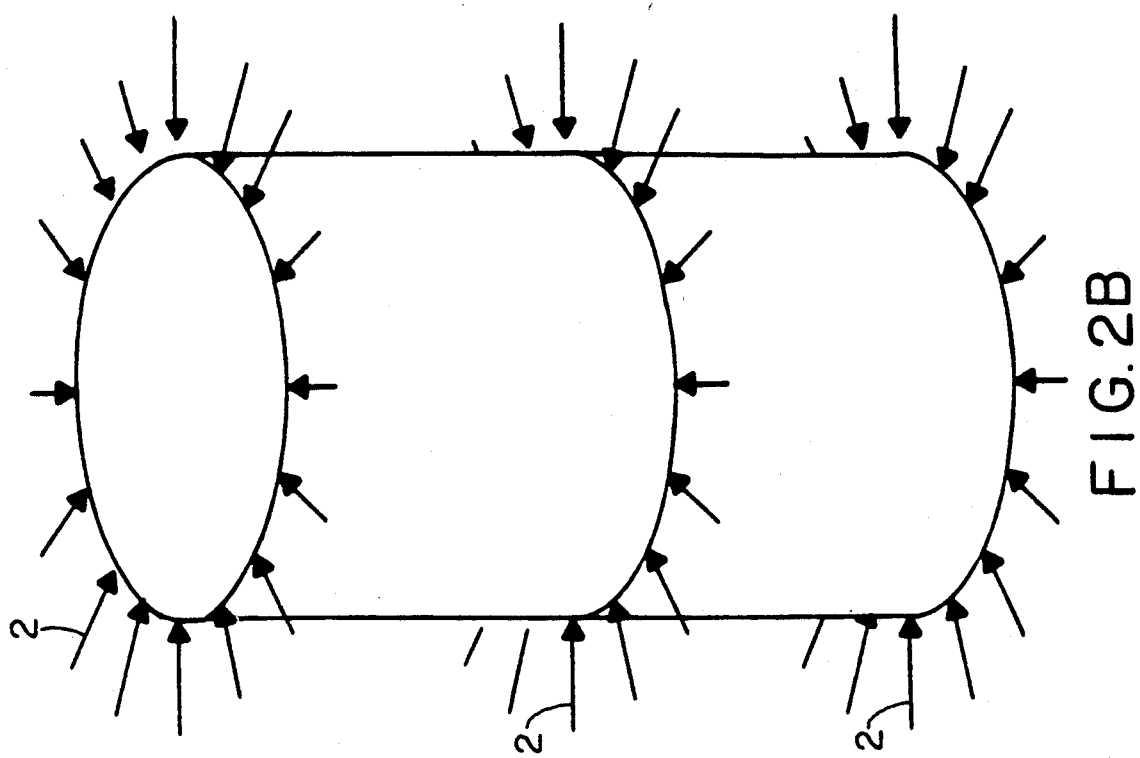
FIG. 2B shows a schematic of fluid bed reactor indicating location of accelerometers along the vertical to measure flow maldistribution within the fluidized bed.
Figure 2A:
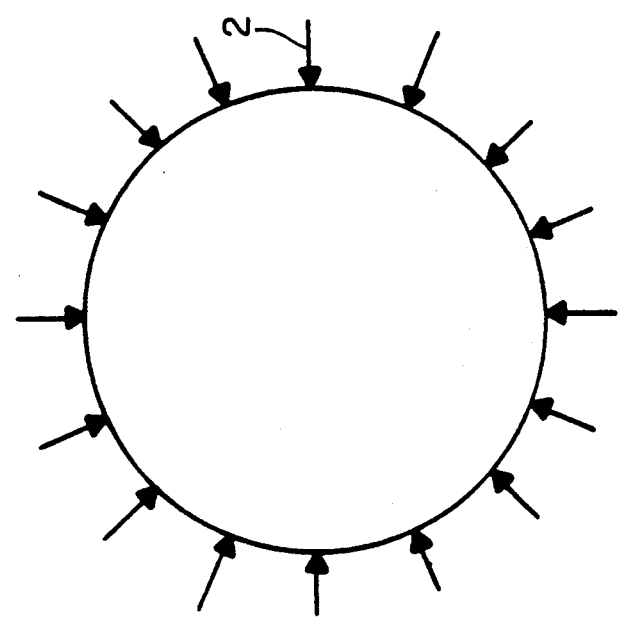
FIG. 2A shows a schematic of fluid bed reactor indicating location of accelerometers in horizontal plane to measure flow maldistribution within the fluidized bed.
Figure 3C:
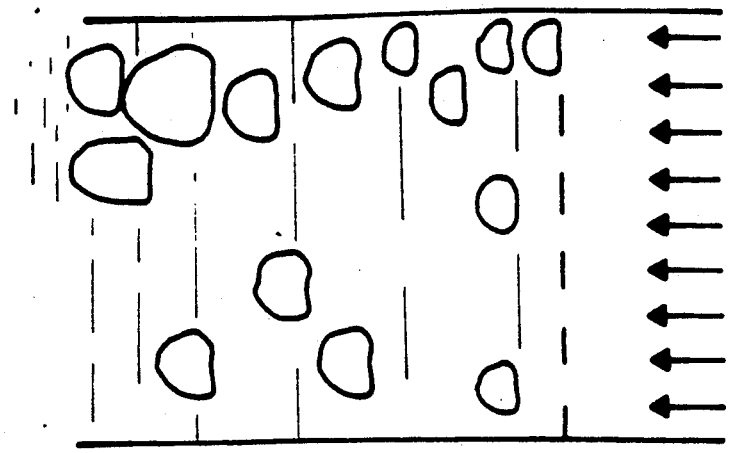
FIGS. 3A, 3B and 3C show a schematic illustration of some flow maldistributions compared to normal flow that can occur in fluidized beds.
Figure 3B:
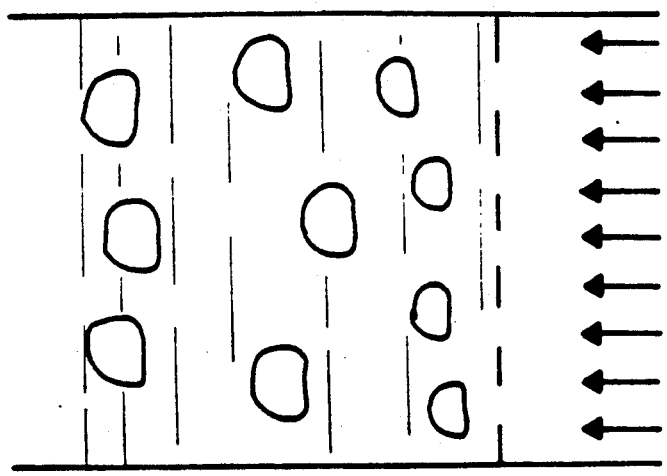
Figure 3A:
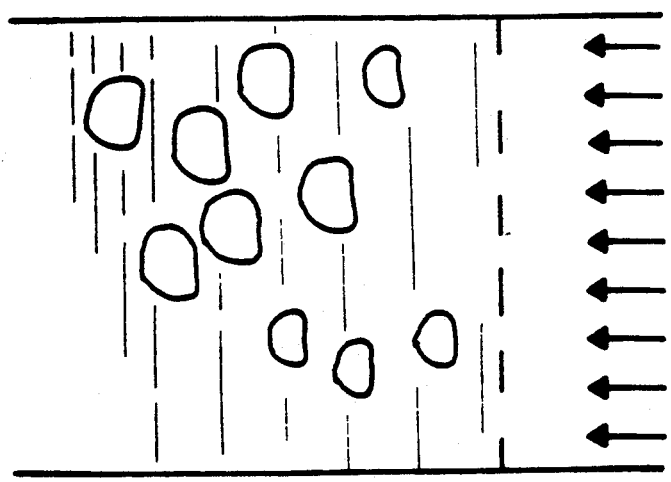
Figure 6:
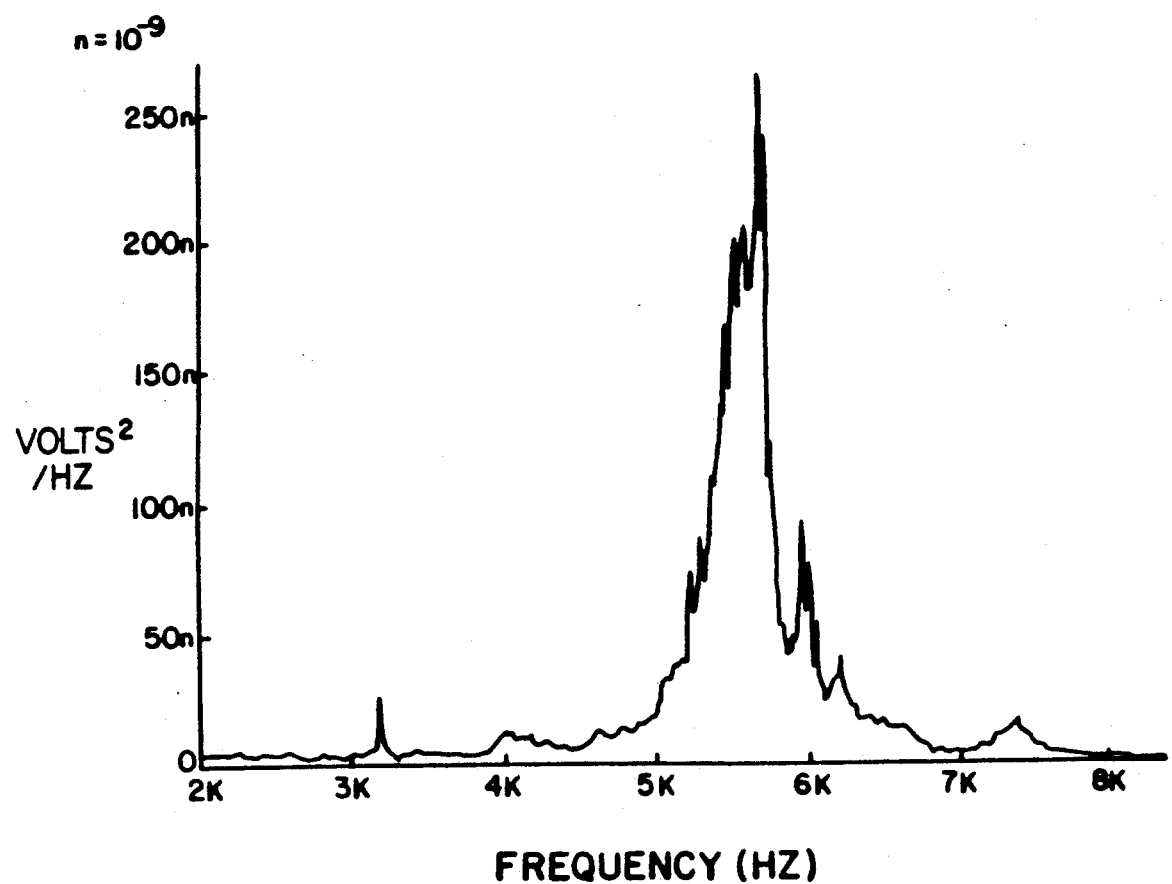
FIG. 6 shows a typical power spectrum from a refractory lined wall and illustrates the location of peak frequency and peak area.

In order to utilize the invention, accelerometers are magnetically or permanently attached to the wall of the vessel which contains a fluidized bed. FIG. 1 shows a schematic diagram of a fluidized bed showing the dense and dilute phases separated by the splash zone. FIGS. 3A, 3B and 3C show a schematic of the various flow states within a fluidized bed. FIG. 3A shows incomplete fluidization in one region of the bed (bed "slump"), FIG. 3B shows normal bubbling in the fluidized bed, and FIG. 3C shows excessive turbulence in the bed arising from poor gas distribution. Flow is indicated by the vertical arrows. The accelerometers 2 are placed circumferentially and vertically around the reactor vessel as shown in FIG. 2. In a series of vertical sections the normal momentum flux of particles to the wall flows through the cross section bounded by that circumference is monitored by the method of the present invention. The electrical signal from the accelerometers, proportional to the wall's normal acceleration, is amplified and transmitted either by cable or optical link to a control room, FIG. 4. In the control room by suitable electronics, the power spectrum is determined as indicated in FIG. 6. The area under the peak may then be determined and is related to flow anisotropy through the bed of the reactor.

Figure 4:
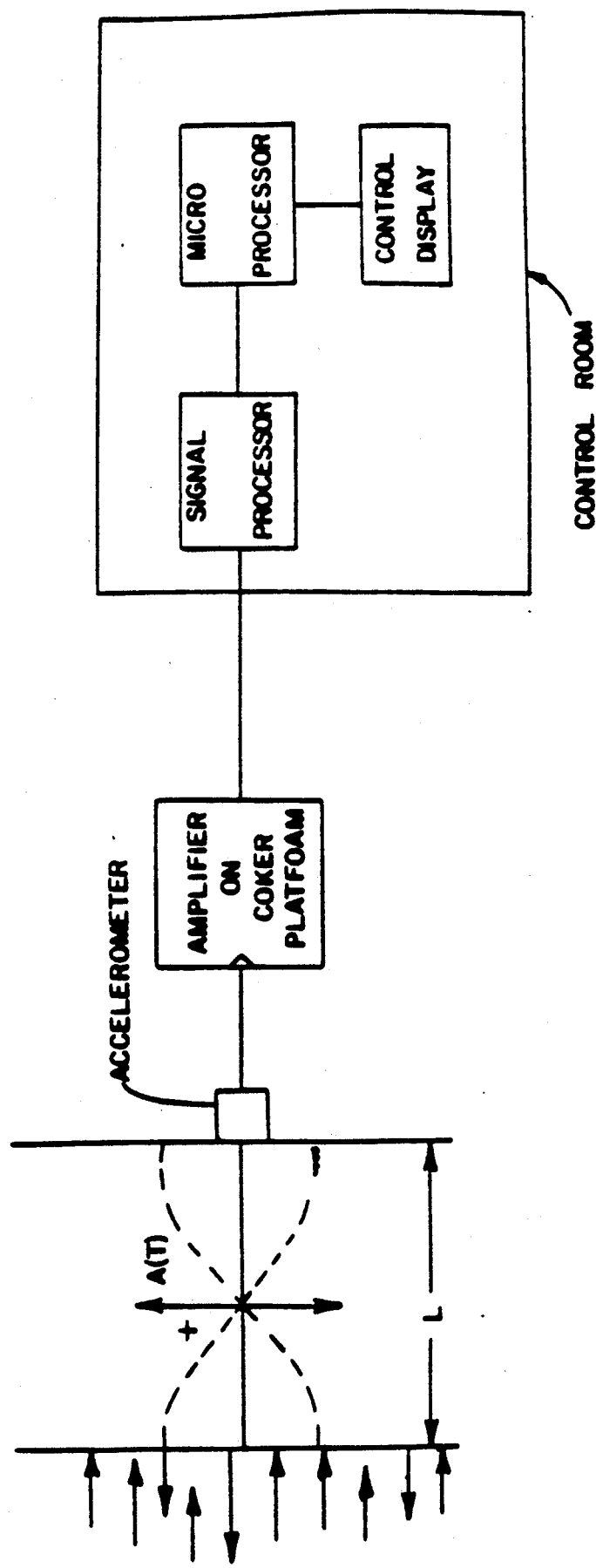
FIG. 4 shows a schematic of the nodes and antinodes of acceleration of a compressional mode wave resonance on a refractory lined wall as well as the coupling between the accelerometer and charge amplifier and the subsequent coupling between the charge amplifier and a signal processor.

FIG. 4 shows a schematic diagram of how the measurement of wall acceleration is made. A magnetically (or otherwise) attached accelerometer (such as a B and K 4384) produces an electrical charge output proportional to the instantaneous acceleration of the wall. This charge is converted by a charge amplifier (such as a B and K 2635) to a voltage output which is again proportional to the normal acceleration of the wall. This voltage is processed by a signal processor (B and K 2032 or equivalent) to produce the power spectrum of the acceleration. The power spectrum of the acceleration of the wall exhibits a peak located at a frequency corresponding to the wall resonance. Both the frequency of this peak and its area can be determined by a suitable computer algorithm.

Figure 5:
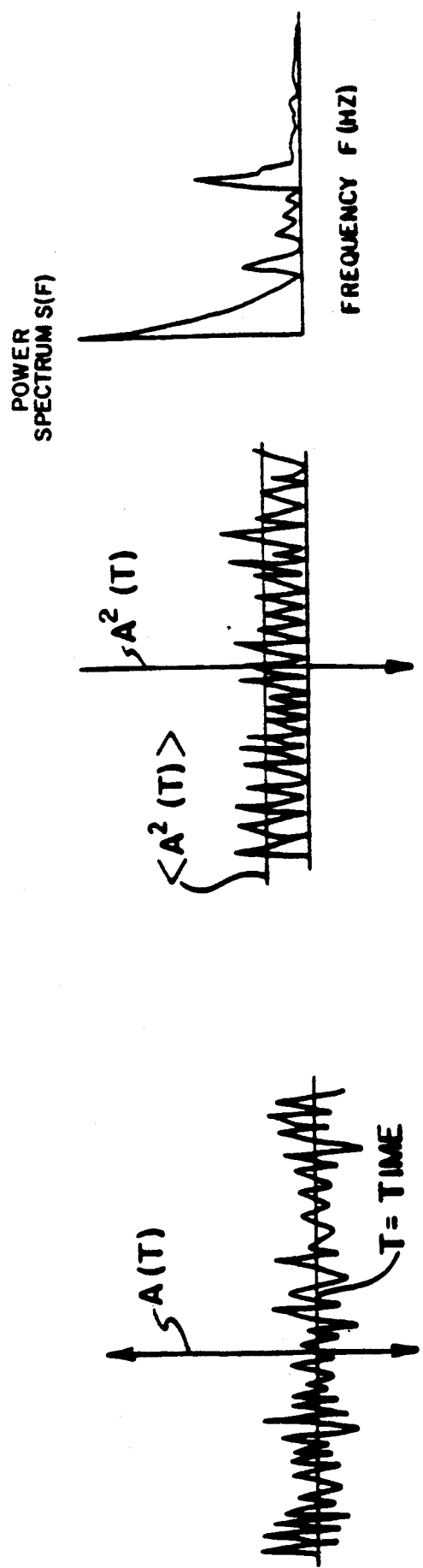
FIGS. 5A, 5B, and 5C illustrate the conversion of a time varying acceleration to a power spectrum.

FIGS. 5A, 5B and 5C exhibit the relationship between the acceleration and its square as a function of time and as a function of frequency. The Power Spectrum for a stationary random function of time displays the mean square acceleration as a function of frequency. The area under the Power Spectrum is one half of the mean square acceleration, $<A^2(T)>$. The mathematical relationship between the power spectrum, S(F), the acceleration, A(T), and time, T, is expressed as follows: mean acceleration $<A(T)>=0$, $<A^2(T)>=2\int S(F)dF$.

FIG. 6 shows a typical power spectrum obtained from an accelerometer placed on a refractory lined wall on a fluid bed regenerator. The frequency and area of the wall resonance is indicated.

FIG. 4 also illustrates the placement of the accelerometer on the wall of the vessel containing the dense bed, and the spatial variation of the acceleration normal to the wall at the fundamental mode of wall vibration. Under these circumstances, for a homogeneous wall, bounded by two media whose density and sound velocity is much less than that of the wall, it is known that the fundamental mode has a node in the center and an antinode at the two boundaries. The frequency of the wall resonance is then simply given by the average compressional sound velocity of the wall divided by twice the thickness of the wall. FIG. 4 also illustrates excitation of the wall resonance, namely the impact of the particles to the fluid bed which produces a steady state wall resonance peak in the power spectrum of the accelerometer output.

Figure 7:
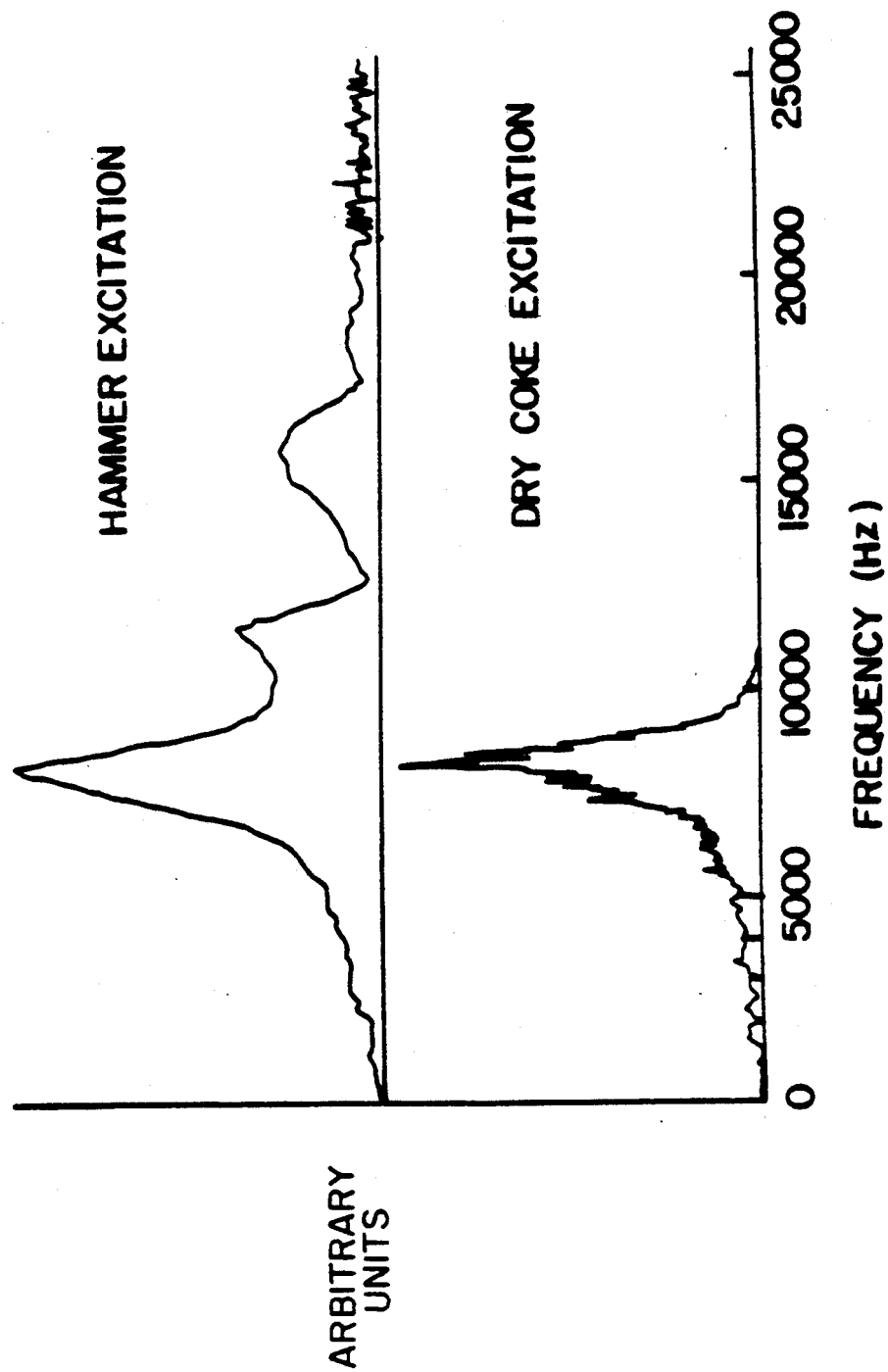
FIG. 7 shows the comparison between the response of the wall to hammer excitation and the response of the wall to particle excitation.

FIG. 7 shows how the wall resonance can be explicitly identified by comparison between the response of the wall to hammer excitation and the response of the wall to particle excitation.

The present invention is a method to monitor flow anisotropy of a two phase fluidized bed by determining the power spectrum of the wall vibrations. Although the method does not depend on any theory, the method may be made plausible by relating the power spectrum to the characteristics of the particles within the unit.

In this invention, it is disclosed that the use of the area of the localized wall resonance can be used to obtain direct information on the flow immediately adjacent to the wall. It can be shown that the area of the wall resonance, A, is given by $$A(M/S^2) = K_1[p_B(1/CM^3)M^2(GM) V_o^3(FT/SEC)]^{\frac{1}{2}} \quad (1)$$

In Eq. (1) the area of the wall resonance A is defined in units of RMS acceleration and is easily obtained by integrating through the wall resonance as displayed in a power spectrum as shown in FIG. 4. The quantity $K_1$ is of the order of 10 to 15 for walls with steel of the order of 0.6 "and refractory of the order of 5". The quantity $K_1$ can be independently determined by hammer excitation or if relative measurements are made, preserved as a constant in the application of Eq. (1). The other quantities in Eq. (1) are:

$p_B$ = volume density of particles in units of number per cm$^3$

M = average mass of a particle in units of grams $V_o$ = normal velocity of particles at wall in units of feet per second Eq. (1) is derived by considering the impact of solid particles within the two phase medium as the equivalent of a random impact of many hammers. It is the vibrational equivalent to the electrical phenomena of "shot noise". Eq. (1) relates an easily measured quantity, A, to properties of the hydrodynamic state of the two phase fluid adjacent to the wall Thus A, coupled to the flow state of the two phase fluid within the fluidized bed or transfer line can be used to monitor the flow state in terms of changes in the quantity $p_B$, M and $V_o$. Large changes in M are unexpected for many petrochemical processes and a major use of the invention is to monitor $p_B$ and $V_o$ at various locations in the bed, and through these measurements get information on flow or turbulence within the bed.

We can recast Eq. (1) in terms of particle diameter d and the mass density of the two phase fluid $p_M$ where $$p_M = p_B M \quad (2)$$

With the substitution of Eq. (2) in Eq. (1) we obtain ($K_2$ is a constant of the order of $1-2 \times 10^{-6}$ for refractory walls approximately 5 "thick lining steel walls approximately 0.5" thick and which again can be obtained by calibration under known flow conditions or by hammer excitation)

$$A(M/S^2) = K_2\{d(u)\}^{3/2}[p_M(\#/FT^3)]^{\frac{1}{2}}V_o(FT/SEC)^{3/2} \quad (3)$$

where u is in microns and # means lbs.

From Eq. (3), if we assume that d, the particle diameter is a constant, we see that the quantity A can be used to monitor $p_M$ or $V_o$.

The equations given above all relate the quantity A, which is measured by determining the area of the wall resonance, to significant features of the two phase flow within the fluidized bed of interest.

If accelerometers are placed circumferentially in a horizontal plane about the reactor, the variation of A from accelerometer to accelerometer supplies information on bed anisotropy such as bed turbulence due to improper distribution of fluidization gas, or regions of bed "slump" through the circumferential variation of $[p_B(1/CM^3)V_o^3-(FT/SEC)]$.

The same method permits estimating other bed anisotropies such as the variation of the bed density, $p_B(1/CM^3)$, through the dense phase if the horizontal array of accelerometers is moved vertically along the reactor. Significant differences in vertical surveys through the dense phase at different points around the circumference can be interpreted as variations in bed density through the dense bed.

An important feature of this invention is the ability to place an accelerometer on the steel shell of a refractory lined vessel or pipe and distinguish the wall resonance from other noise peaks and resonances. Distinguishing the wall resonance can be accomplished easily if it is the dominant peak, it falls at the frequency expected from prior knowledge of the thickness of the wall or by the use of hammer excitation. Once the wall resonance is identified in the power spectrum, its area determines the quantity A and can be used, as above to determine certain features of the state of the two phase fluid within the vessel or pipe. The constant $K_1$ can be determined by hammer measurements and the theory.

Some of the differences from prior art are: (1) the fact that the measurement is non-intrusive requiring no modification of the vessel or pipe (fluffy insulation might have to be separated from the steel or other metal shell); (2) that it is passive, utilizing vibrational or acoustic noise generated within the process vessel or pipe, not externally generated sound or vibrations; (3) that the frequency range of the measurements is in the range imposed by the wall resonance, hence essentially low frequencies compared to those utilized in "ultrasonic" flow measurements. Another way of looking at this difference is that the wavelength of the vibrational measurements is of the order of the dimensions of the wall, whereas in ultrasonic measurements the wave length is considerably smaller than the dimension of the wall. Due to this observation the measurement process described in this patent is relatively immune to inhomogenities if the wall which would seriously effect any ultrasonic measurement.

EXAMPLE 1

Flow Maldistribution Within a Fluidized Bed

One can determine if there is appreciable flow maldistribution within a fluidized bed by the following steps:

As shown in FIG. 2, locations are marked on the vessel containing the fluidized bed: circumferentially at a constant level from the grid of the bed. One or more such horizontal sections are located in the dense phase of the bed below the "bed level".

Accelerometers are placed in contact with the locations and mounted either magnetically or bolted to permanent tabs.

As shown in FIG. 4, the output of the accelerometer is led to a charge amplifier or other suitable impedance converting and amplifying device. The output of the charge amplifier is the input to either a portable signal processor on the platform, or to a recording system and then to a signal processor.

The power spectrum is displayed on either the portable system, or from the recorded data, and the wall resonance identified as discussed in a copending application Ser. No. 072,533, now U.S. Pat. No. 4,877,488.

The area of the wall resonance, A, is obtained and its variation with angle at one or more vertical heights above the grid of the fluidized bed.

From Eq. (3) of the text it is seen that A is a strong function of the normal particle velocity and a relatively weak function of the mass density in the fluidized bed.

Figure 8:
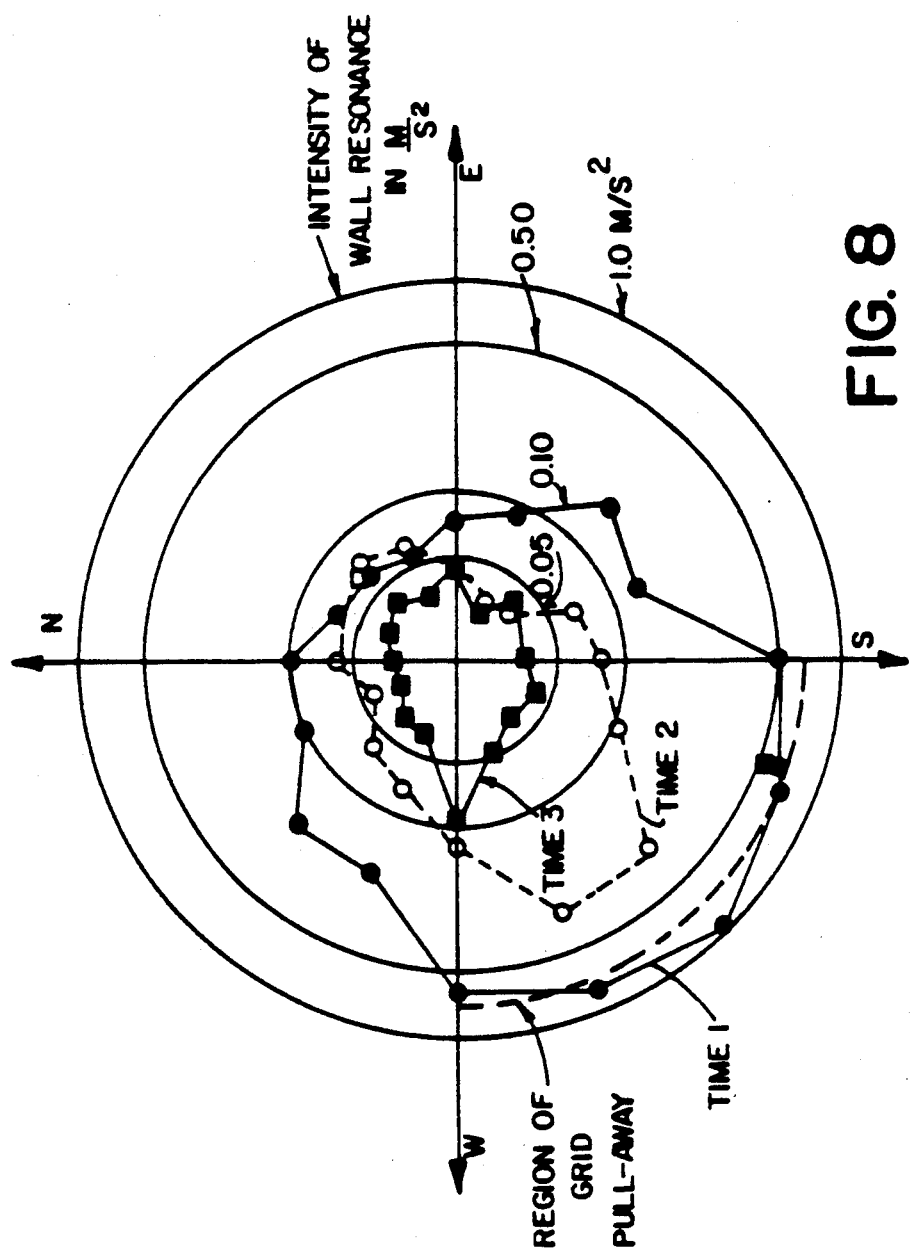
FIG. 8 shows the logarithm of magnitude of the RMS acceleration within the wall resonance on a regenerator as a function of direction about the unit under three different states of flow within the fluidized bed.

In FIG. 8 we see the results of a series of circumferential measurements on a fluidized bed regenerator of catalytic cracking unit. The regenerator includes a grid bonded to walls of the regenerator. The measurements of the area of the wall resonance, A, are shown on a polar plot at various times over a period of one year. The radius of the polar plot is taken proportional to the logarithm of the quantity A.

FIG. 8 is easily interpreted in terms of turbulence due to:

(a) At time 1 when the grid was pulled away from the wall and an excessive gas flow of turbulent stream of oxygen was streaming up the southwest quadrant. The large anisotropy exhibited in the southwest quadrant illustrates the ability of the passive acoustics process to pinpoint a region of high turbulence within a fluidized bed.

(b) At time 2 when the mechanical status of the grid had worsened to the extent that "torch oil" had to be injected into the unit at the location indicated by the arrow in order to reduce the injection of oxygen into upper regions of the regenerator and reduce excessive temperature gradients across the bed. This curve illustrates the sensitivity of the passive acoustics process to changes in flow conditions.

(c) At time 3 when the grid had been replaced, its attachment to the walls of the unit repaired, and flow within the regenerator restored to normal uniform conditions. The uniformity of flow within the unit is shown by the small angular variation in the area of the wall resonance.

In the above example, the passive acoustic information was used to pinpoint the location of large gas influx into the bed (see FIG. 2) for correction by torch oil combustion in an interim stage and repair of the mechanical defect during shutdown. The large variation in A for the data at time 1 between the northeast and southwest quadrants (a factor of 20) is consistent with Eq. (3) and the large value of $V_o$ in a region of turbulence due to excessive gas flow.

EXAMPLE 2

Flow Maldistribution Within a Fluid Bed Coker

Figure 9:
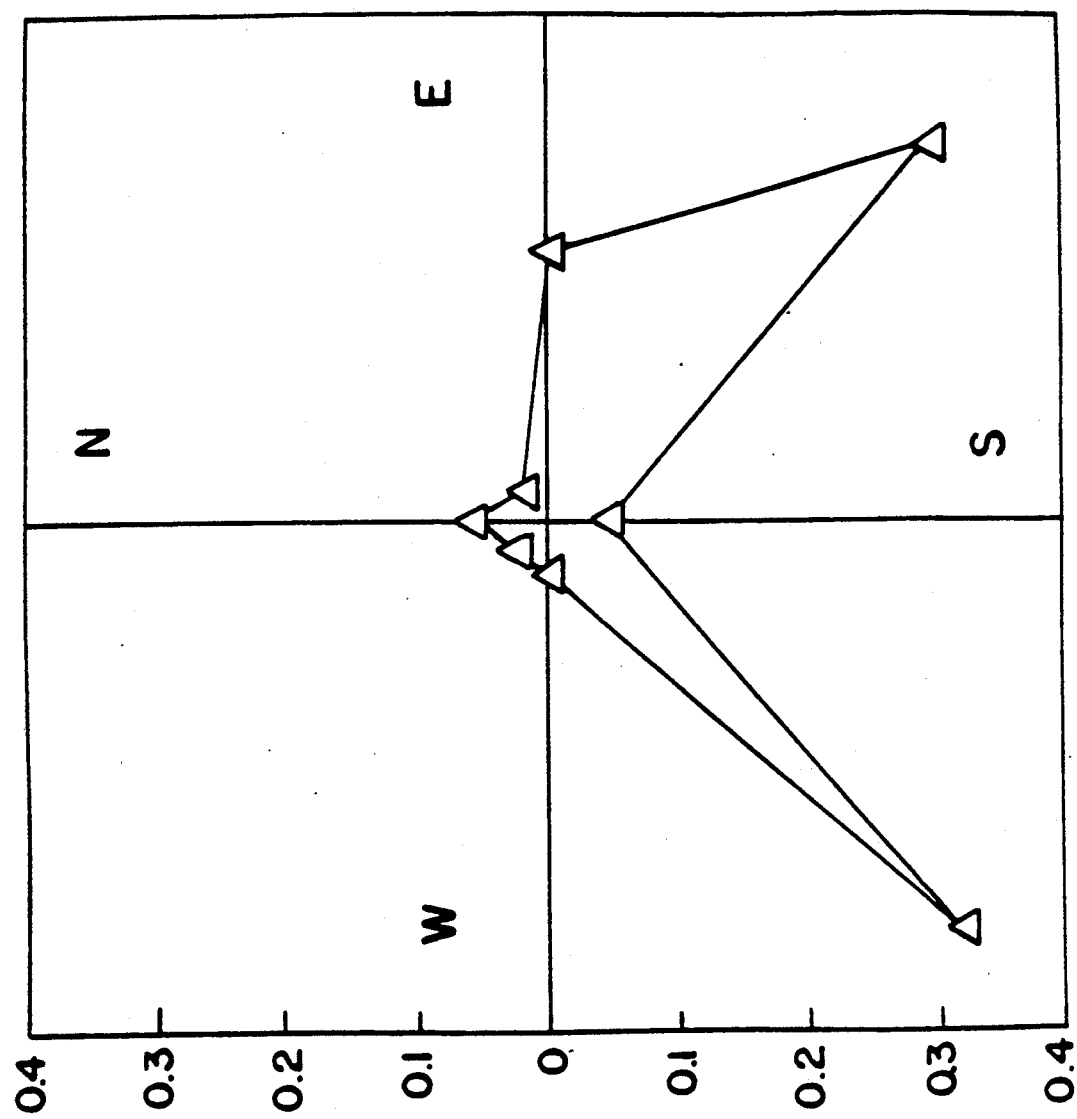
FIG. 9 shows a polar plot of the area of the wall resonance (m/s$^2$) of a coker, under conditions when flow through the sheds was blocked.

Example shows blocked flow in a fluid bed coker. FIG. 9 is a polar plot of the quantity A (m/s$^2$) as a function of angle taken clockwise from north (90=east, 180=south, 270=west) circumferentially in the "sheds" region near the bottom of a fluid bed coker. Flow was blocked and information was needed on the region of flow blockage, so that steam lances could be directed to the region in order to clear the obstruction by pulverization. Pulverizing steam injected into the region of the northwest quadrant where the RMS acceleration was wow, eliminated the obstruction illustrating the point that the vibrational data is sufficient to pinpoint a region of flow maldistribution.

From the polar plot it is seen that the northwest quadrant of the reactor exhibits a significantly smaller signal than the other quadrants suggesting that the obstruction was located in this quadrant. Subsequent steam lancing in this quadrant eliminated the obstruction and the unit returned to normal operations.

It is interesting to note that in this case, the wall resonance dominates the entire spectrum.

Figure 10:
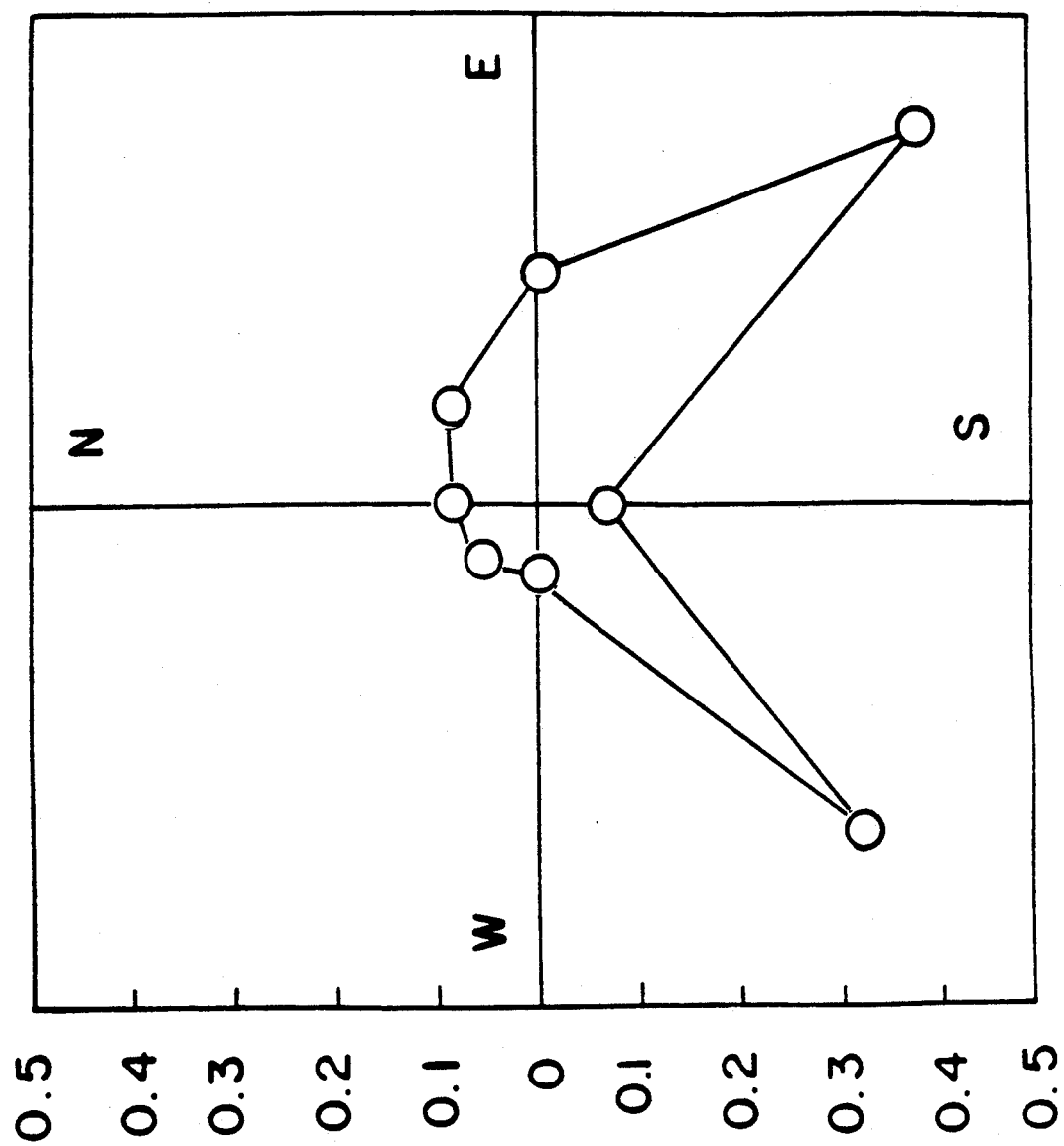
FIG. 10 shows a polar plot of the total RMS acceleration (m/s$^2$) over a 25.6 kHz bandwidth for the same locations shown in FIG. 9.

FIG. 10 shows a polar plot of the total RMS acceleration (m,s$^2$) over a 25.6 kHz bandwidth for the same locations shown in FIG. 8. This data illustrates the point that under the circumstances when the wall resonance is the dominant contributor to the power spectrum, it is not necessary to use its area to pinpoint the region of low particle activity.

Figure 11:
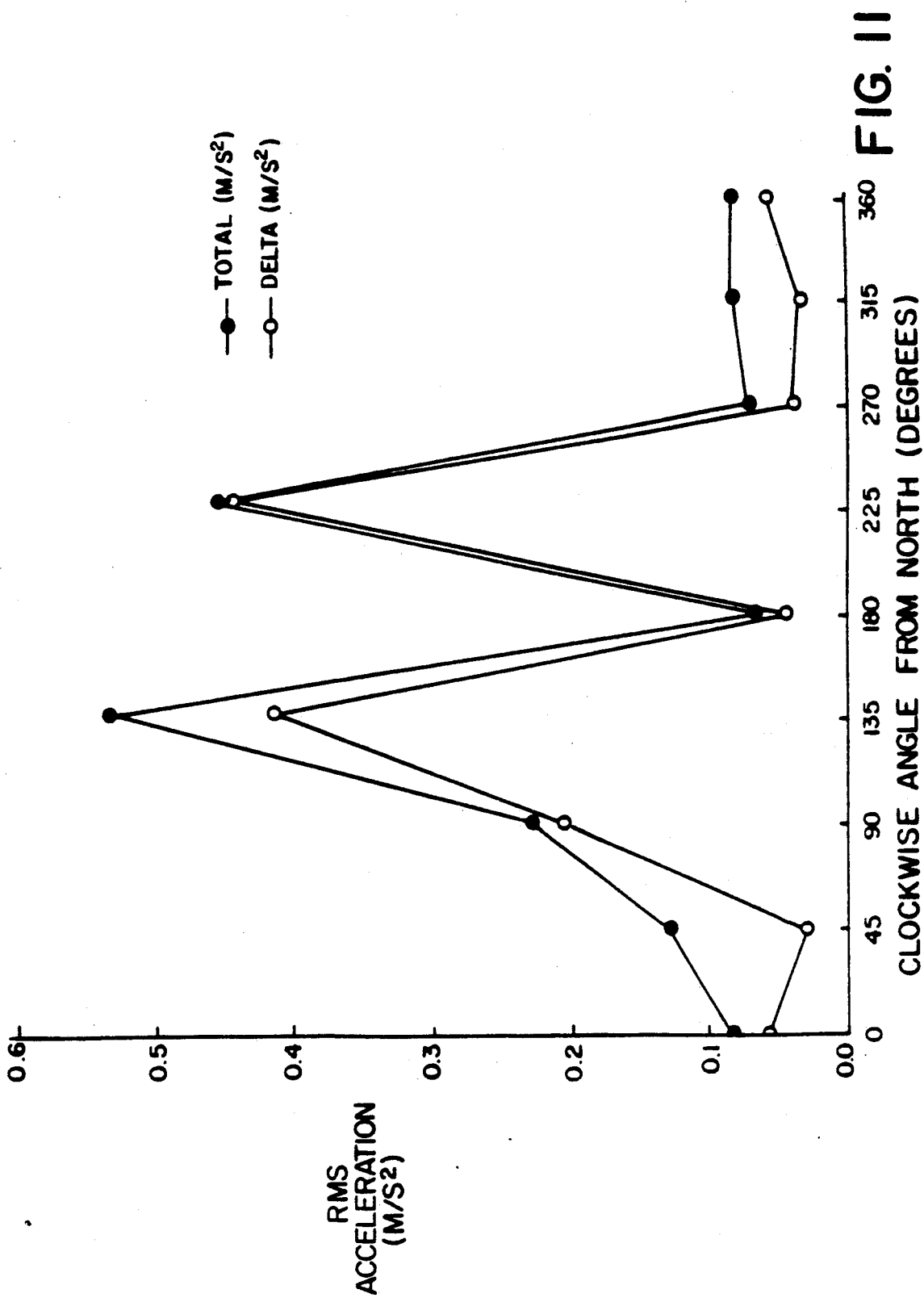
FIG. 11 shows the comparison of the area of the power spectrum over the wall resonance and that over a 25.6 kHz band for the measurements shown in FIGS. 9 and 10.

FIG. 11 shows the comparison of the area of the power spectrum over the wall resonance and that over a 25.6 kHz band for the measurements shown in FIG. 8 and 9.

In practice the process described herein for monitoring flow conditions with a fluidized bed would proceed as follows:

(a) Obtain a base line polar plot of the unit right after startup when it is known that the flow within the bed is uniform (base case).

(b) Monitor the accelerometer locations on a periodic basis to determine flow maldistribution and prepare polar plots for comparison with the above base case.

(c) Monitor the accelerometer locations when other information indicates the possibility of flow maldistribution, or after remedial efforts have been made to eliminate flow blockage and compare the obtained polar plot with the base case.

The method may be extended to determine flow anisotropy in the vertical direction by determining the power spectrum as a function of frequency for another set of wall vibrations taken at positions circumferentially about the reactor but spaced vertically from the first positions (see FIG. 3). The area of the power spectrum under a resonance peak for each of the second measurements is determined. Then the area of the power spectrum between adjacent first measurements is compared with the change between the area of the power spectrum between corresponding adjacent second positions. The differences between the changes in the area of the power spectrum correspond to a change in bed density. This follows because the area of the power spectrum, A, depends on both density and velocity. This change in density also indicates bed flow anisotropy.

What is claimed is:

1. A method for the non-intrusive determination of flow anisotropy through a two phase fluid bed in a structure comprising:
    (a) measuring wall vibrations of said structure and then determining the power spectrum as a function of frequency, said wall vibrations taken at several first positions circumferentially about the structure,
    (b) determining the area of the power spectrum which includes a resonance peak for each of said first positions,
    (c) correlating a change in said area between adjacent first positions of the power spectrum with flow anisotropy through the cross-section of said structure bounded by the circumference including said several first positions.

2. The method of claim 1 wherein said structure is a fluid bed coker reactor.

3. The method of claim 1 wherein said structure is a fluidized bed catalytic cracker.

4. The method of claim 1 wherein said step of measuring wall vibrations is performed by using an accelerometer.

5. The method of claim 1 for the non-intrusive determination of flow anisotropy through a two phase fluid bed in a structure further comprising the steps of
  (a) measuring wall vibrations of said structure and then determining the power spectrum as a function of frequency, said wall vibrations taken at several second positions circumferentially about the structure, said second positions spaced vertically from said first positions in said structure,
  (b) determining the area of the power spectrum which includes a resonance peak for each of said second positions,
  (c) comparing a change in said area of said power spectrum between adjacent first positions with the change between said area of said power spectrum between corresponding second positions and correlating difference between the changes in said area of the power spectrum with a change in bed density.

* * * * *